United States Patent [19]

Chaudhuri

[11] Patent Number: 5,437,809
[45] Date of Patent: Aug. 1, 1995

[54] SHAMPOO COMPOSITIONS WITH DIMETHICONE COPOLYOLS

[75] Inventor: Dwaipayan Chaudhuri, deceased, late of Windsor, Great Britain, by Shelia Chaudhuri, legal representative

[73] Assignee: The Gillette Company, Boston, Mass.

[21] Appl. No.: 74,821

[22] PCT Filed: Dec. 11, 1991

[86] PCT No.: PCT/US91/09245
§ 371 Date: Sep. 9, 1993
§ 102(e) Date: Sep. 9, 1993

[87] PCT Pub. No.: WO92/10990
PCT Pub. Date: Jul. 9, 1992

[30] Foreign Application Priority Data

Dec. 18, 1990 [GB] United Kingdom ............... 9027363

[51] Int. Cl.$^6$ .................... C11D 1/02; C11D 1/82; C11D 1/83; C11D 1/94
[52] U.S. Cl. .................... 252/174.15; 252/547; 252/174.21; 252/DIG. 1; 252/DIG. 7; 252/DIG. 13
[58] Field of Search ........... 252/DIG. 1, 174.15, 252/174.21, DIG. 13, 547, DIG. 7; 424/70.12, 70.121, 70.22, 70.28, 70.31

[56] References Cited

U.S. PATENT DOCUMENTS

| | | | |
|---|---|---|---|
| 4,311,695 | 1/1982 | Starch | 424/184 |
| 4,656,043 | 4/1987 | Hawkins et al. | 424/70 |
| 4,704,272 | 11/1987 | Oh et al. | 424/70 |
| 4,707,293 | 11/1987 | Ferro | 252/DIG. 13 |
| 4,741,855 | 5/1988 | Grote et al. | 252/DIG. 13 |
| 4,772,427 | 9/1988 | Dawson et al. | 252/DIG. 13 |
| 4,788,006 | 11/1988 | Bolich et al. | 252/DIG. 13 |
| 4,902,499 | 2/1990 | Bolisk | 424/70 |
| 5,104,645 | 4/1992 | Cardin et al. | 252/DIG. 13 |

FOREIGN PATENT DOCUMENTS 2192194 1/1988 United Kingdom .
2196980 5/1988 United Kingdom .

*Primary Examiner*—Paul Lieberman
*Assistant Examiner*—Douglas J. McGinty
*Attorney, Agent, or Firm*—Stephen P. Williams

[57] ABSTRACT

A conditioning shampoo composition comprises, as the conditioning agents thereof, from 0.1 to 4.0% by weight of one or more dimethicone copolyols having an ethylene oxide/propylene oxide (EO/PO) ratio of from 20/80 to 80/20 and from 0.5 to 4.0% by weight of one or more non-ionic emulsifiers having an HLB of from 8 to 12 and which do not affect the foaming property of the shampoo.

7 Claims, No Drawings

SHAMPOO COMPOSITIONS WITH DIMETHICONE COPOLYOLS

This invention is concerned with shampoo compositions and, more particularly, with conditioning shampoos, that is shampoos which have both the usual cleansing action and also a conditioning action. The use of such shampoos avoids the necessity for the separate use of a hair conditioner after the hair has been washed with a conventional shampoo having only a cleansing action.

Whilst conditioning shampoo compositions are known, a disadvantage that arises with some of them is that on repeated use, there is a build up of the conditioning ingredients on the hair so that the washed hair no longer feels pleasant to the user.

Conditioning shampoos have also been described and are commercially available which do not suffer from this disadvantage, that is the build up of conditioning agents. Such shampoo compositions are described for example, in U.S. Pat. Nos. 4,704,272; 4,741,855; and 4,788,006 and in British Specifications 2,192,194A and 2,196,980A.

An object of the present invention is to provide alternative conditioning shampoo compositions which are not subject to the significant build up of conditioning ingredients on repeated use.

We have found that these requirements can be met by using a combination of certain dimethicone copolyols and certain non-ionic emulsifiers having an HLB of from 8 to 12 as the conditioning agents in a shampoo composition which may, in other respects, be conventional.

According to the present invention, there is provided a conditioning shampoo composition which comprises, as the conditioning agents thereof, from 0.1 to 4.0% by weight of one or more dimethicone copolyols having an ethylene oxide/propylene oxide (EO/PO) ratio of from 20/80 to 80/20 and from 0.5 to 4.0% by weight of one or more non-ionic emulsifiers having an HLB of from 8 to 12 and which do not affect the foaming property of the shampoo.

Dimethicone copolyol is a CTFA adopted name for polysiloxane polyether copolymers of the formula:

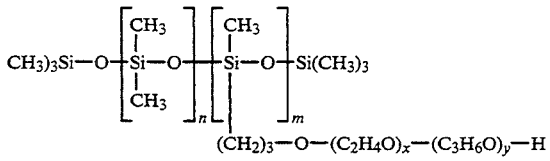

$$(CH_2)_3-O-(C_2H_4O)_x-(C_3H_6O)_y-H$$

where n, m, x and y are integers. The dimethicone copolyols used according to the invention have values of x and y such that the ratio x:y, that is the EO/PO ratio, is from 20/80 to 80/20.

Preferred dimethicone copolyols contain from 60 to 140 $SiO_2$ units, that is the sum of n and m is from 60 to 140.

The dimethicone copolyol constituent of the shampoo composition preferably comprises a major proportion of a dimethicone copolyol having an EO/PO ratio of from 80/20 to 70/30 and a minor proportion of a dimethicone copolyol having an EO/PO ratio of from 20/80 to 40/60.

Suitable dimethicone copolyols for use in the shampoo compositions according to the invention are available, for example, from Th. Goldschmidt AG, of Essen, Germany under the Trade Mark "Abil". A preferred dimethicone copolyol having an EO/PO ratio of 77/23 is available as "Abil" B88183 and a preferred dimethicone copolyol having an EO/PO ratio of 20/80 is available as "Abil" B8852; these two materials both contain about 60 $SiO_2$ units. A preferred dimethicone copolyol having an EO/PO ratio of 40/60 and containing about 140 $SiO_2$ units is available as "Abil" G911.

We have found that the extent of deposition of the dimethicone copolyol can be controlled by using it in conjunction with the non-ionic emulsifier having an HLB of from 8 to 12; in this way excessive build up of the conditioning agent on repeated use of the shampoo can be prevented. The greater the amount of the non-ionic emulsifier used, in relation to a given amount of dimethicone copolyol, the less of the latter is left on the hair.

For any particular choice of dimethicone copolyol(s) and non-ionic emulsifier(s), the optimum proportions of these two ingredients to obtain the desired deposition of dimethicone copolyol on the hair can be readily established by routine experimentation. By way of example, using a preferred combination of dimethicone copolyols as referred to above and the particularly preferred non-ionic emulsifier referred to below, we have found that an optimum level of dimethicone copolyol deposition is obtained by using 1.5% by weight of the non-ionic emulsifier and 1.1% by weight of the dimethicone copolyol combination.

Preferred non-ionic emulsifiers having an HLB of from 8 to 12 for use in accordance with the invention are:

| CTFA name | Trade name | Chemical name | HLB |
|---|---|---|---|
| Sorbitan laurate | Arlacel 20 | Sorbitol mono-laurate | 8.6 |
| PEG30 castor oil | Arlatone 827 | Ethoxylated castor oil | 11.9 |
| PEG25 hydrogenated castor oil | Arlatone G | POE(25) hydrogenated castor oil | 10.8 |
| PEG40 sorbitan peroleate | Arlatone T | POE(40) sorbitol haptaoleate | 9.5 |
| PEG40 sorbitan hexaoleate | Atlas G1086 | POE(40) sorbitol hexaoleate | 10.2 |
| n/a | Atlas G1087 | POE sorbitol oleate | 10.2 |
| n/a | Atlas G1096 | POE sorbitol hexaoleate | 11.4 |
| n/a | Atlas G1281 | POE triglyceride | 9.7 | n/a = not available. (All supplied by ICI Speciality Chemicals).

Of these, PEG40 sorbitan hexaoleate is particularly preferred.

The shampoo composition according to the invention will contain cleansing agents which may be any of the anionic, cationic, amphoteric and non-ionic surfactants conventionally used in such compositions, these ingredients being used in the conventional proportions. The composition can, and usually will, contain further ingredients which provide particular desired characteristics or properties to the composition.

Suitable ingredients for shampoo compositions according to the invention are, for example, as follows:

Cleansing agents

It is preferred that the cationic component of the surfactants included in the composition should be one or more quaternary ammonium salt surfactants. A number of quaternary surfactants can be used for this purpose; preferred compounds are, for example, stearamidopropyl dimethylamine lactate and steartrimonium hydrolysed animal protein (available under the Trade Mark "Crotein Q" from Croda Chemicals).

The proportion of quaternary surfactant used is preferably from 0.5 to 2.0% by weight.

It is preferred that the composition should contain from 10 to 20% by weight of one or more anionic surfactants, such as sodium laureth sulphate and ammonium lauryl sulphate, and from 1 to 5% by weight of one more amphoteric surfactants, such as cocamidopropyl betaine, as the main cleansing agents, Thickeners Suitable thickeners include, for example, hydroxypropyl methyl cellulose and talloweth 60 myristyl glycol; the proportion of thickener is suitably from 0.1 to 2.0% by weight, depending on the type of thickener used and the required viscosity. Hair bodying agents Suitable agents for imparting body to the hair include, for example, cetyl alcohol and lauric acid monoglyceride; these agents are suitably used in a proportion of from 0.50 to 1.50% by weight.

Other conventional ingredients which may be and preferably are included in the shampoo composition are: a hydrotrope, such as ammonium xylene sulphonate, to prevent deposition in hard water areas of undesirable materials on the hair; pearlising agents; preservatives; pH adjusters, such as lactic acid; colourants; and perfumes.

In order that the invention may be more fully understood, the following examples, in which all percentages are by weight, are given by way of illustration only.

EXAMPLES 1-3

Three conditioning shampoo compositions were made up having the compositions set out in Table 1.

TABLE 1

| Example | % active | | |
|---|---|---|---|
| | 1 | 2 | 3 |
| Sodium laureth sulphate | 7.00 | 7.00 | 7.00 |
| Ammonium lauryl sulphate | 7.00 | 7.00 | 7.00 |
| Cocamidopropyl betaine | 1.60 | 1.60 | 1.60 |
| Ammonium xylene sulphonate | 1.40 | 1.40 | 1.40 |
| PEG40 sorbitan hexaoleate | 1.50 | 1.50 | 1.50 |
| Dimethicone copolyol (Abil B88183) | 1.00 | 1.00 | 1.00 |
| Dimethicone copolyol (Abil B8852) | 1.10 | 1.10 | — |
| Dimethicone copolyol (Abil G911) | — | — | 0.10 |
| Stearamidopropyl dimethylamine lactate | 0.625 | 0.625 | 0.625 |
| Cetyl alcohol | 0.50 | 0.50 | 0.50 |
| Na laureth sulphate (and) glycol distearate (and) cocamide MEA | 0.90 | 0.90 | 0.90 |
| Hydroxypropyl methyl cellulose | 0.25 | 0.25 | 0.25 |
| Methylchloroisothiazolinone | 0.0009 | 0.0009 | 0.0009 |
| Talloweth 60 myristyl glycol | 0.45 | — | — |
| Lauric acid monoglyceride | — | 1.50 | 1.50 |
| Lactic acid | — | 0.20 | 0.20 |
| Colour, perfume and water | to 100 | to 100 | to 100 |

These shampoo compositions were used by a professional hairdresser to wash hair in comparison with a commercially available conditioning shampoo (used as a control).

Each person having their hair washed had one half of their head (left or right) washed with one of the test shampoos and the other half washed with the control shampoo. The shampoos, that is the test shampoo and the control shampoo, were provided to the hairdresser in syringes containing 7 ml of shampoo. The syringes were labelled with the test persons name, date, time of appointment and side of head on which the shampoo was to be used. Neither the test person nor the hairdresser knew which shampoo (that is test shampoo or control shampoo) was present in each syringe.

Each test shampoo was tested on a panel of 60 subjects.

During and after the hair washing operation, the hairdresser made an assessment on both sides of the head using a five point scale (5=excellent, 4=very good, 3=good, 2=fair and 1=poor) for each of the following fifteen attributes:

initial lather
quantity of lather
quality of lather
cleanliness of wet hair
ease of rinsing
ease of wet combing
ease of dry combing
flyaway
hair manageability
softness
silkiness
condition of hair
body
feel of dry hair
shine The average ratings of the shampoo of Example 1 over the whole of the test panel were in the range 4.06-5.00, those of the shampoo of Example 2 were in the range 4.28-5.00, and those of the shampoo of Example 3 were in the range 4.32-5.0 (for comparison the ratings of the control shampoo were in the range 4.24-5.00).

It is claimed:

1. A conditioning shampoo composition which comprises in percent by weight in water 10 to 20% of one or more anionic surfactants, 1 to 5% of one or more amphoteric surfactants, 0.5 to 2.0% of one or more quaternary ammonium surfactants, 0.5 to 4.0% of one or more non-ionic emulsifiers having an HLB of from 8 to 12, and 0.1 to 4.0% of one or more dimethicone copolyols having from 60 to 140 $SiO_2$ units and an ethylene oxide/propylene oxide (EO/PO) ratio of from 20/80 to 80/20.

2. A shampoo composition according to claim 1 wherein the dimethicone copolyol comprises a major proportion of a dimethicone copolyol having an EO/PO ratio of from 80/20 to 70/30 and a minor proportion of a dimethicone copolyol having an EO/PO ratio of from 20/80 to 40/60.

3. A shampoo composition according to claim 2 comprising 1.1% dimethicone copolyol and 1.5% non-ionic emulsifier.

4. A shampoo composition according to claim 1, in which the non-ionic emulsifier having an HLB of from 8 to 12 is polyethylene glycol (PEG) 40 sorbitan hexaoleate.

5. A shampoo composition according to claim 1 in which the dimethicone coplyol has an EO/PO ratio of 77/33.

6. A shampoo composition according to claim 1, in which the quaternary surfactant is stearamidopropyl dimethylamine lactate or steartrimonium hydrolysed animal protein.

7. A shampoo composition according to claim 1 comprising 1.1% dimethicone copolyol and 1.5% non-ionic emulsifier.

* * * * *